United States Patent [19]
Racie et al.

[11] Patent Number: 6,084,071
[45] Date of Patent: Jul. 4, 2000

[54] HUMAN L105 POLYPEPTIDES AND POLYNUCLEOTIDES ENCODING SAME

[75] Inventors: Lisa A. Racie, Acton; Kenneth Jacobs, Newton; Zhijian Lu, Bedford; Edward R. LaVallie, Harvard; John M. McCoy, Reading, all of Mass.

[73] Assignee: Genetics Institute, Cambridge, Mass.

[21] Appl. No.: 09/094,287

[22] Filed: Jun. 9, 1998

Related U.S. Application Data

[60] Provisional application No. 60/090,101, Jun. 11, 1997.

[51] Int. Cl.⁷ .......................... C07K 14/52; A61K 38/19; C12N 15/19
[52] U.S. Cl. .......................... 530/351; 424/85.1; 514/2; 514/8; 514/12; 536/23.5; 930/140; 435/69.5; 435/71.1; 435/71.2; 435/325; 435/252.3; 435/320.1; 435/471
[58] Field of Search .......................... 530/351; 424/85.1; 514/2, 8, 12; 536/23.5; 930/140; 435/69.5, 71.1, 71.2, 325, 252.3, 320.1, 471

[56] References Cited

U.S. PATENT DOCUMENTS 5,707,829  1/1998  Jacobs et al. .......................... 435/69.1

FOREIGN PATENT DOCUMENTS

WO 96/06169  2/1996  WIPO .
WO 96/25497  8/1996  WIPO .
WO 97/07198  2/1997  WIPO .

OTHER PUBLICATIONS

Cullen et al. (1989) Endocrinology, vol. 125 pp. 1774–1782.
Rieger et al. Glossary of Genetics & Cytogenetics. Springer–Verlag 4th Edition, 1976.
Jose et al., 1994, Biochem. Biophys. Res. Comm. 205: 788–794.
Hillier et al., GenBank accession No. AA151607, May 14, 1997.
Nomiyama, H. (Reference 1) and Nagira et al. (Reference 2), GenBank accession No. AB002409, Aug. 15, 1997.
Petrenko and Enrietto, GenBank accesion No. L34553, Jul. 14, 1994.
Bandman et al., GeneSeq accession No. T33528, May 2, 1997.
Bandman et al., GeneSeq accession No. W00668, May 2, 1997.

*Primary Examiner*—Prema Mertz
*Attorney, Agent, or Firm*—Lahive & Cockfield, LLP; Amy E. Mandragouras, Esq.; Peter C. Lauro, Esq.

[57] ABSTRACT

A chemokine, human L105, is disclosed.

10 Claims, No Drawings

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 908 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (ix) FEATURE:
      (A) NAME/KEY: CDS
      (B) LOCATION: 80..481

(ix) FEATURE:
      (A) NAME/KEY: mat_peptide
      (B) LOCATION: 149..481

(xi) SEQUENCE DESCRIPTION: SEQ ID NO:1:

```
GAATTCGGCC AAAGAGGCCT ACTTGCAGCT GCCCACCTCA CCCTCAGCTC TGGCCTCTGT     60

CTCACCCTCT ACCACAGACA TGGCTCAGTC ACTGGCTCTG AGCCTCCTTA TCCTGGTTCT    120

GGCCTTTGGC ATCCCCAGGA CCCAAGGCAG TGATGGAGGG GCTCAGGACT GTTGCCTCAA    180

GTACAGCCAA AGGAAGATTC CCGCCAAGGT TGTCCGCAGC TACCGGAAGC AGGAACCAAG    240

CTTAGGCTGC TCCATCCCAG CTATCCTGTT CTTGCCCCGC AAGCGCTCTC AGGCAGAGCT    300

ATGTGCAGAC CCAAAGGAGC TCTGGGTGCA GCAGCTGATG CAGCATCTGG ACAAGACACC    360

ATCCCCACAG AAACCAGCCC AGGGCTGCAG GAAGGACAGG GGGGCCTCCA AGACTGGCAA    420

GAAAGGAAAG GGCTCCAAAG GCTGCAAGAG GACTGAGCGG TCACAGACCC CTAAAGGGCC    480

ATAGCCCAGT GAGCAGCCTG GAGCCCTGGA GACCCCACCA GCCTCACCAG CGCTTGAAGC    540

CTGAACCCAA GATGCAAGAA GGAGGCTATG CTCAGGGGCC CTGGAGCAGC CACCCCATGC    600

TGGCCTTGCC ACACTCTTTC TCCTGCTTTA ACCACCCCAT CTGCATTCCC AGCTCTACCC    660

TGCATGGCTG AGCTGCCCAC AGCAGGCCAG GTCCAGAGAG ACCGAGGAGG GAGAGTCTCC    720

CAGGGAGCAT GAGAGGAGGC AGCAGGACTG TCCCCTTGAA GGAGAATCAT CAGGACCCTG    780

GACCTGATAC GGCTCCCCAG TACACCCCAC CTCTTCCTTG TAAATATGAT TTATACCTAA    840

CTGAATAAAA AGCTGTTCTG TCTTCCCACC CAAAAAAAAA AAAAAATTGA ATTCTAGACC    900

TGCGGCCG                                                             908
```

(2) INFORMATION FOR SEQ ID NO:2:

(i) SEQUENCE CHARACTERISTICS:
      (A) LENGTH: 134 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:2:

```
Met Ala Gln Ser Leu Ala Leu Ser Leu Leu Ile Leu Val Leu Ala Phe
  1               5                  10                  15

Gly Ile Pro Arg Thr Gln Gly Ser Asp Gly Gly Ala Gln Asp Cys Cys
```

-continued

```
              20                  25                  30
Leu Lys Tyr Ser Gln Arg Lys Ile Pro Ala Lys Val Val Arg Ser Tyr
             35                  40                  45
Arg Lys Gln Glu Pro Ser Leu Gly Cys Ser Ile Pro Ala Ile Leu Phe
 50                  55                  60
Leu Pro Arg Lys Arg Ser Gln Ala Glu Leu Cys Ala Asp Pro Lys Glu
 65                  70                  75                  80
Leu Trp Val Gln Gln Leu Met Gln His Leu Asp Lys Thr Pro Ser Pro
                     85                  90                  95
Gln Lys Pro Ala Gln Gly Cys Arg Lys Asp Arg Gly Ala Ser Lys Thr
                100                 105                 110
Gly Lys Lys Gly Lys Gly Ser Lys Gly Cys Lys Arg Thr Glu Arg Ser
            115                 120                 125
Gln Thr Pro Lys Gly Pro
            130
```

(2) INFORMATION FOR SEQ ID NO:3:

(i) SEQUENCE CHARACTERISTICS:
        (A) LENGTH: 932 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 85..519

(ix) FEATURE:
        (A) NAME/KEY: mat_peptide
        (B) LOCATION: 154..519

(xi) SEQUENCE DESCRIPTION: SEQ ID NO:3:

```
GAATTCGGCC AAAGAGGCCT ACCCAACTTG CAGCTGCCCA CCTCACCCTC AGCTCTGGCC     60
TCTTACTCAC CCTCTACCAC AGACATGGCT CAGTCACTGG CTCTGAGCCT CCTTATCCTG    120
GTTCTGGCCT TTGGCATCCC CAGGACCCAA GGCAGTGATG AGGGGCTCA GGACTGTTGC     180
CTCAAGTACA GCCAAAGGAA GATTCCCGCC AAGGTTGTCC GCAGCTACCG GAAGCAGGAA    240
CCAAGCTTAG GCTGCTCCAT CCCAGCTATC CTGTTCTTGC CCCGCAAGCG CTCTCAGGCA    300
GAGCTATGTG CAGACCCAAA GGAGCTCTGG GTGCAGCAGC TGATGCAGCA TCTGGACAAG    360
ACACCATCCC CACAGAAACC AGCCCAGGGC TGCAGGAAGG ACAGGGGGGC CTCCAAGACT    420
GGCAAGAAAG GAAAGGGCTC CAAAGGCTGC AAGAGTCAGC CCCTCACACC CCTCTTCTGC    480
CCTCACAGGA CTGAGCGGTC ACAGACCCCT AAAGGGCCAT AGCCCAGTGA GCAGCCTGGA    540
GCCCTGGAGA CCCCACCAGC CTCACCAGCG CTTGAAGCCT GAACCCAAGA TGCAAGAAGG    600
AGGCTATGCT CAGGGGCCCT GGAGCAGCCA CCCCATGCTG GCCTTGCCAC ACTCTTTCTC    660
CTGCTTTAAC CACCCCATCT GCATTCCCAG CTCTACCCTG CATGGCTGAG CTGCCCACAG    720
CAGGCCAGGT CCAGAGAGAC CGAGGAGGGA GAGTCTCCCA GGGAGCATGA GAGGAGGCAG    780
CAGGACTGTC CCCTTGAAGG AGAATCATCA GGACCCTGGA CCTGATACGG CTCCCCAGTA    840
CACCCCACCT CTTCCTTGTA AATATGATTT ATACCTAACT GAATAAAAAG CTGTTCTGTC    900
TTCCACCCAA AAAAAAAAA AAAAGCGGCC GC                                    932
```

(2) INFORMATION FOR SEQ ID NO:4:

(i) SEQUENCE CHARACTERISTICS:
    (A) LENGTH: 145 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:4:

```
Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
            35                  40                  45

Arg Lys Gln Glu Pro Ser Leu Gly Cys Ser Ile Pro Ala Ile Leu Phe
50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Ser Gln Pro Leu Thr
            115                 120                 125

Pro Leu Phe Cys Pro His Arg Thr Glu Arg Ser Gln Thr Pro Lys Gly
    130                 135                 140

Pro
145
```

(2) INFORMATION FOR SEQ ID NO:5:

(i) SEQUENCE CHARACTERISTICS:
    (A) LENGTH: 588 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (ix) FEATURE:
    (A) NAME/KEY: CDS
    (B) LOCATION: 76..474

(xi) SEQUENCE DESCRIPTION: SEQ ID NO:5:

```
CGGCCAAAGA GGCCTAAAACT TGCGGCTGTC CATCTCACCT ACAGCTCTGG TCTCATCCTC        60

AACTCAACCA CAATC ATG GCT CAG ATG ATG ACT CTG AGC CTC CTT AGC CTG        111
               Met Ala Gln Met Met Thr Leu Ser Leu Leu Ser Leu
                 1               5                  10

GTC CTG GCT CTC TGC ATC CCC TGG ACC CAA GGC AGT GAT GGA GGG GGT        159
Val Leu Ala Leu Cys Ile Pro Trp Thr Gln Gly Ser Asp Gly Gly Gly
            15                  20                  25

CAG GAC TGC TGC CTT AAG TAC AGC CAG AAG AAA ATT CCC TAC AGT ATT        207
Gln Asp Cys Cys Leu Lys Tyr Ser Gln Lys Lys Ile Pro Tyr Ser Ile
        30                  35                  40

GTC CGA GGC TAT AGG AAG CAA GAA CCA AGT TTA GGC TGT CCC ATC CCG        255
Val Arg Gly Tyr Arg Lys Gln Glu Pro Ser Leu Gly Cys Pro Ile Pro
45                  50                  55                  60

GCA ATC CTG TTC TCA CCC CGG AAG CAC TCT AAG CCT GAG CTA TGT GCA        303
Ala Ile Leu Phe Ser Pro Arg Lys His Ser Lys Pro Glu Leu Cys Ala
```

-continued

```
                       65                    70                    75
AAC CCT GAG GAA GGC TGG GTG CAG AAC CTG ATG CGC CGC CTG GAC CAG        351
Asn Pro Glu Glu Gly Trp Val Gln Asn Leu Met Arg Arg Leu Asp Gln
                80                    85                    90

CCT CCA GCC CCA GGG AAA CAA AGC CCC GGC TGC AGG AAG AAC CGG GGA        399
Pro Pro Ala Pro Gly Lys Gln Ser Pro Gly Cys Arg Lys Asn Arg Gly
        95                   100                   105

ACC TCT AAG TCT GGA AAG AAA GGA AAG GGC TCC AAG GGC TGC AAG AGA        447
Thr Ser Lys Ser Gly Lys Lys Gly Lys Gly Ser Lys Gly Cys Lys Arg
        110                   115                   120

ACT GAA CAG ACA CAG CCC TCA AGA GGA TAGCCCAGTA GCCCGCCTGG              494
Thr Glu Gln Thr Gln Pro Ser Arg Gly
125                   130

AGCCCAGGAG ATCCCCCACG AACTTCAAGC TGGGTGGTTC ACGGTCCAAC TCACAGGCAA      554

AGAGGGAGCT AGAAAACAGA CTCAGGAGCC GCTA                                  588

(2) INFORMATION FOR SEQ ID NO:6:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Gln Met Met Thr Leu Ser Leu Leu Ser Leu Val Leu Ala Leu
 1               5                   10                  15

Cys Ile Pro Trp Thr Gln Gly Ser Asp Gly Gly Gln Asp Cys Cys
                20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Ser Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
            115                 120                 125

Gln Pro Ser Arg Gly
            130

(2) INFORMATION FOR SEQ ID NO:7:

(i) SEQUENCE CHARACTERISTICS:
        (A) LENGTH: 187 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "EST sequence"

(xi) SEQUENCE DESCRIPTION: SEQ ID NO:7:

CAGACATGGC TCAGTCACTG GCTCTGAGCC TCCTTATCCT GGTTCTNGCC TATGNAATCC       60

CCAGGACCCA AGGCAGTGAT GGAGGGGCTC AGGACTGTTG CCTCAAGTAC AGCCAAAGGA      120
```

-continued

```
AGATTCCCGC CAAGGTTGTC CGCAGCTACC GGAAGCAGGA ACCAAGCTTA GGCTGCTCCA        180

TCCCAGC                                                                 187

(2) INFORMATION FOR SEQ ID NO:8:

(i) SEQUENCE CHARACTERISTICS:
        (A) LENGTH: 535 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "EST sequence"

(xi) SEQUENCE DESCRIPTION: SEQ ID NO:8:

CAGTCACTGG CTCTGAGCCT CCTTATCCTG GTTCTGGCCT TTGNATCCCC AGGACCCAAG         60

GCAGTGATGG AGGGGCTCAG GACTGTTGCC TCAAGTACAG CCAAAGGAAG ATTCCCGCCA        120

AGGTTGTCCG CAGCTACCGG AAGCAGGAAC CAAGCTTAGG CTGCTCCATC CCAGCTATCC       180

TGTTCTTGCC CCGCAAGCGC TCTCAGGCAG AGCTATGTGC AGACCCAAAG GAGCTCTGGG       240

TGCAGCAGCT GATGCAGCAT CTGGACAAGA CACCATCCCC ACAGAAACCA GCCCAGGGTG       300

CAGGAAGGAC AGGGGGGCCT CCAAGACTGG CAAGAAAGGA AAGGGCTCCA AAGGCTGCAA       360

GAGGACTGAG CGGTCACAGA CCCTAAAGGG CCATAGCCAG TGAGCAGCTG GAGCCTGGAG       420

ACCCACCAGC TNACAGCGTT GAANCTGAAC CAAGATNCAA GAAGGAGGTA TNTCAGGGGC       480

CTGGANAGCA CCCATGTGGC TTCANATCTT TGTCTGTTTA CACCCATTGA TTCAG            535

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:9:

CNTCCATCAC TGCCTTGGGT CCTGGGGAT                                           29
```

HUMAN L105 POLYPEPTIDES AND POLYNUCLEOTIDES ENCODING SAME

This application is a continuation-in-part of application Ser. No. 60/090,101 (converted to a provisional application from non-provisional application Ser. No. 08/872,704), filed Jun. 11, 1997, which is incorporated by reference herein.

FIELD OF THE INVENTION

The present invention provides chemokines called human L105 proteins and polynucleotides encoding them.

BACKGROUND OF THE INVENTION

Chemokines are a subclass of cytokines which cause the directed migration or chemotaxis of particular cell populations either to or away from higher concentrations of the chemokine. Many chemokines have been identified which cause migration of major blood cell populations. These factors may be useful for directing the migration of cell populations to areas of desired action or away from areas of unwanted action. It would, therefore, be desirable to identify new chemokines and polynucleotides encoding them.

Applicants' U.S. Pat. No. 5,707,829 and published international patent application WO97/07198 disclose a novel murine chemokine identified as "L105." Murine L105 has been demonstrated to have chemokinetic/chemoattractant activity for several cell types, including thymocytes, kidney mesangial cells and lymphocytes localized in lymph nodes. Because of these beneficial activities, it would be desirable to identify human homologues of murine L105.

SUMMARY

In one embodiment, the present invention provides a composition comprising an isolated polynucleotide selected from the group consisting of:

(a) a polynucleotide comprising the nucleotide sequence of SEQ ID NO:1 from nucleotide 80 to nucleotide 481;

(b) a polynucleotide comprising the nucleotide sequence of SEQ ID NO:1 from nucleotide 149 to nucleotide 481;

(c) a polynucleotide comprising a fragment of the nucleotide sequence of SEQ ID NO:1 encoding a protein having chemokine activity;

(d) a polynucleotide encoding a protein comprising the amino acid sequence of SEQ ID NO:2;

(e) a polynucleotide encoding a protein comprising the amino acid sequence of SEQ ID NO:2 from amino acid 14 to amino acid 134;

(f) a polynucleotide encoding a protein comprising a fragment of the amino acid sequence of SEQ ID NO:2 having chemokine activity;

(g) a polynucleotide which is an alielic variant of SEQ ID NO:1;

(h) a polynucleotide comprising the nucleotide sequence of SEQ ID NO:3 from nucleotide 85 to nucleotide 519;

(i) a polynucleotide comprising the nucleotide sequence of SEQ ID NO:3 from nucleotide 124 to nucleotide 519;

(j) a polynucleotide comprising a fragment of the nucleotide sequence of SEQ ID NO:3 encoding a protein having chemokine activity;

(k) a polynucleotide encoding a protein comprising the amino acid sequence of SEQ ID NO:4;

(l) a polynucleotide encoding a protein comprising the amino acid sequence of SEQ ID NO:4 from amino acid 14 to amino acid 145;

(m) a polynucleotide encoding a protein comprising a fragment of the amino acid sequence of SEQ ID NO:4 having chemokine activity;

(n) a polynucleotide which is an allelic variant of SEQ ID NO:3; and (o) a polynucleotide capable of hybridizing to any one of the polynucleotides specified in (a), (b), (d), (e), (h), (i), (k) or (l) above.

Preferably, such polynucleotide comprises the nucleotide sequence of SEQ ID NO:1 from nucleotide 80 to nucleotide 481; the nucleotide sequence of SEQ ID NO:1 from nucleotide 119 to nucleotide 481; the nucleotide sequence of the full-length protein coding sequence of clone huL105_3 deposited under accession number ATCC 98429; or the nucleotide sequence of a mature protein coding sequence of clone huL105_3 deposited under accession number ATCC 98429. In other preferred embodiments, the polynucleotide encodes the full-length or a mature protein encoded by the cDNA insert of clone huL105_3 deposited under accession number ATCC 98429. In further preferred embodiments, the present invention provides a polynucleotide encoding a protein comprising a fragment of the amino acid sequence of SEQ ID NO:2 having chemokine activity, the fragment preferably comprising eight (more preferably twenty, most preferably thirty) consecutive amino acids of SEQ ID NO:2, or a polynucleotide encoding a protein comprising a fragment of the amino acid sequence of SEQ ID NO:2 having chemokine activity, the fragment comprising the amino acid sequence from amino acid 62 to amino acid 71 of SEQ ID NO:2.

Preferably, such polynucleotide comprises the nucleotide sequence of SEQ ID NO:3 from nucleotide 85 to nucleotide 519; the nucleotide sequence of SEQ ID NO:3 from nucleotide 124 to nucleotide 519; the nucleotide sequence of the full-length protein coding sequence of clone huL105_7 deposited under accession number ATCC 98431; or the nucleotide sequence of a mature protein coding sequence of clone huL105_7 deposited under accession number ATCC 98431. In other preferred embodiments, the polynucleotide encodes the full-length or a mature protein encoded by the cDNA insert of clone huL105_7 deposited under accession number ATCC 98431. In yet other preferred embodiments, the present invention provides a polynucleotide encoding a protein comprising the amino acid sequence of SEQ ID NO:4 from amino acid 124 to amino acid 134. In further preferred embodiments, the present invention provides a polynucleotide encoding a protein comprising a fragment of the amino acid sequence of SEQ ID NO:4 having chemokine activity, the fragment preferably comprising eight (more preferably twenty, most preferably thirty) consecutive amino acids of SEQ ID NO:4, or a polynucleotide encoding a protein comprising a fragment of the amino acid sequence of SEQ ID NO:4 having chemokine activity, the fragment comprising the amino acid sequence from amino acid 67 to amino acid 76 of SEQ ID NO:4.

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing a protein, which comprise:

(a) growing a culture of the host cell transformed with such polynucleotide compositions in a suitable culture medium; and (b) purifying the protein from the culture.

The protein produced according to such methods is also provided by the present invention.

Other embodiments provide an isolated gene corresponding to the cDNA sequence of SEQ ID NO:1, and an isolated gene corresponding to the cDNA sequence of SEQ ID NO:3. Also provided by the present invention are organisms that have enhanced, reduced, or modified expression of the gene(s) corresponding to the polynucleotide sequences disclosed herein.

Compositions comprising a protein having chemokine activity are also disclosed. In preferred embodiments the protein comprises an amino acid sequence selected from the group consisting of:

(a) the amino acid sequence of SEQ ID NO:2;
(b) the amino acid sequence of SEQ ID NO:2 from amino acid 14 to amino acid 134;
(c) fragments of the amino acid sequence of SEQ ID NO:2 having chemokine activity;
(d) the amino acid sequence of SEQ ID NO:4;
(e) the amino acid sequence of SEQ ID NO:4 from amino acid 14 to amino acid 145; and
(f) fragments of the amino acid sequence of SEQ ID NO:4 having chemokine activity;

the protein being substantially free from other mammalian proteins.

Preferably such protein comprises the amino acid sequence of SEQ ID NO:2, or the amino acid sequence of SEQ ID NO:2 from amino acid 14 to amino acid 134. In further preferred embodiments, the present invention provides a protein comprising a fragment of the amino acid sequence of SEQ ID NO:2 having chemokine activity, the fragment preferably comprising eight (more preferably twenty, most preferably thirty) consecutive amino acids of SEQ ID NO:2, or a protein comprising a fragment of the amino acid sequence of SEQ ID NO:2 having chemokine activity, the fragment comprising the amino acid sequence from amino acid 62 to amino acid 71 of SEQ ID NO:2.

Preferably such protein comprises the amino acid sequence of SEQ ID NO:4, the amino acid sequence of SEQ ID NO:4 from amino acid 124 to amino acid 134, or the amino acid sequence of SEQ ID NO:4 from amino acid 14 to amino acid 145. In further preferred embodiments, the present invention provides a protein comprising a fragment of the amino acid sequence of SEQ ID NO:4 having chemokine activity, the fragment preferably comprising eight (more preferably twenty, most preferably thirty) consecutive amino acids of SEQ ID NO:4, or a protein comprising a fragment of the amino acid sequence of SEQ ID NO:4 having chemokine activity, the fragment comprising the amino acid sequence from amino acid 67 to amino acid 76 of SEQ ID NO:4.

Such compositions may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

DETAILED DESCRIPTION

The sequence for the human L105 was found in the Genbank EST database by searching using the murine L105 sequence (polynucleotide, SEQ ID NO:5; protein, SEQ ID NO:6). The search revealed two possible related human ESTs, AA027314 (SEQ ID NO:7) and W17274 (SEQ ID NO:8), which partially overlapped.

A probe of sequence CXTCCATCACTGCCTTGGGTC-CTGGGGAT (X=biotin) (SEQ ID NO:9) was designed to isolate a full-length human L105 clone. The probe was used to screen a human adult heart cDNA library. The screening revealed two full-length clones, which were identified as "huL105_3" and "huL105_7".

The polynucleotide and amino acid sequences of huL105_3 are reported as SEQ ID NO:1 and SEQ ID NO:2, respectively. The coding sequence of huL105_3 includes nucleotides 80–481, which encode a 134 amino acid full-length protein. The mature protein begins at amino acid 14 (SEQ ID NO:2).

The polynucleotide and amino acid sequences of huL105_7 are reported as SEQ ID NO:3 and SEQ ID NO:4, respectively. The coding sequence of huL105_7 includes nucleotides 85–519, which encode a 145 amino acid full-length protein. The mature protein begins at amino acid 14 (SEQ ID NO:4).

Comparison of huL105_3 and huL105_7 reveals that huL105_7 contains an insertion relative to huL105_3. The inserted region is found at nucleotides 454–486 of SEQ ID NO:3. This region encodes additional amino acids 124–134 in SEQ ID NO:4.

huL105_3 and huL105_7 cDNAs were deposited on May 9, 1997 under the Budapest Treaty with the American Type Culture Collection (10801 University Boulevard, Manassas, Va. 20110-2209 U.S.A.) and were assigned accession numbers ATCC 98429 and ATCC 98431, respectively. All restrictions on the availability to the public of the deposited material will be irrevocably removed upon the granting of the patent, except for the requirements specified in 37 C.F.R. § 1.808(b), and the term of the deposit will comply with 37 C.F.R. § 1.806.

Comparison of the human L105 sequences (SEQ ID NO:2 and SEQ ID NO:4) to the murine L105 sequence (SEQ ID NO:6) confirms that these proteins are human homologues of the murine chemokine. As a result, the human L105 proteins share the chemokinetic activities of murine L105.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form of such protein may be obtained by expression of the disclosed full-length polynucleotide (preferably those deposited with ATCC) in a suitable mammalian cell or other host cell. The sequence of the mature form of the protein may also be determinable from the amino acid sequence of the full-length form.

The present invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

Organisms that have enhanced, reduced, or modified expression of the gene(s) corresponding to the polynucleotide sequences disclosed herein are provided. The desired change in gene expression can be achieved through the use of antisense polynucleotides or ribozymes that bind and/or cleave the mRNA transcribed from the gene (Albert and Morris, 1994, *Trends Pharmacol. Sci.* 15(7): 250–254; Lavarosky et al., 1997, *Biochem. Mol. Med.* 62(1): 11–22; and Hampel, 1998, *Prog. Nucleic Acid Res. Mol. Biol.* 58: 1–39; all of which are incorporated by reference herein). Transgenic animals that have multiple copies of the gene(s) corresponding to the polynucleotide sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, *Bioessays* 14(9): 629–633; Zwaal et al., 1993, *Proc. Natl. Acad. Sci. USA* 90(16): 7431–7435; Clark et al., 1994, *Proc. Natl. Acad. Sci. USA* 91(2): 719–722; all of which are incorporated by reference herein), or through homologous recombination, preferably detected by positive/negative genetic selection strategies (Mansour et al., 1988, *Nature* 336:348–352; U.S. Pat. Nos. 5,464,764; 5,487,992; 5,627,059; 5,631,153; 5,614,396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the protein product(s) of the corresponding gene(s).

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

Species homolonues of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide. Preferably, polynucleotide species homologues have at least 60% sequence identity (more preferably, at least 75% identity; most preferably at least 90% identity) with the given polynucleotide, and protein species homologues have at least 30% sequence identity (more preferably, at least 45% identity; most preferably at least 60% identity) with the given protein, where sequence identity is determined by comparing the nucleotide sequences of the polynucleotides or the amino acid sequences of the proteins when aligned so as to maximize overlap and identity while minimizing sequence gaps. Species homologues may be isolated and identified by making suitable probes or primers from the sequences provided herein and screening a suitable nucleic acid source from the desired species. Preferably, species homologues are those isolated from mammalian species. Most preferably, species homologues are those isolated from certain mammalian species such as, for example, *Pan troglodytes, Gorilla gorilla, Pongo pygmaeus, Hylobates concolor, Macaca mulatta, Papio papio, Papio hamadryas, Cercopithecus aethiops, Cebus capucinus, Aotus trivirgatus, Sanguinus oedipus, Microcebus murinus, Mus musculus, Rattus norvegicus, Cricetulus griseus, Felis catus, Mustela vison, Canis familiaris, Oryctolagus cuniculus, Bos taurus, Ovis aries, Sus scrofa,* and *Equus caballus,* for which genetic maps have been created allowing the identification of syntenic relationships between the genomic organization of genes in one species and the genomic organization of the related genes in another species (O'Brien and Seuánez, 1988, *Ann. Rev. Genet.* 22: 323–351; O'Brien et al., 1993, *Nature Genetics* 3:103–112; Johansson et al., 1995, *Genomics* 25: 682–690; Lyons et al., 1997, *Nature Genetics* 15: 47–56; O'Brien et al., 1997, *Trends in Genetics* 13(10): 393–399; Carver and Stubbs, 1997, *Genome Research* 7:1123–1137; all of which are incorporated by reference herein).

The invention also encompasses allelic variants of the disclosed polynucleotides or proteins; that is, naturally-occurring alternative forms of the isolated polynucleotides which also encode proteins which are identical or have significantly similar sequences to those encoded by the disclosed polynucleotides. Preferably, allelic variants have at least 60% sequence identity (more preferably, at least 75% identity; most preferably at least 90% identity) with the given polynucleotide, where sequence identity is determined by comparing the nucleotide sequences of the polynucleotides when aligned so as to maximize overlap and identity while minimizing sequence gaps. Allelic variants may be isolated and identified by making suitable probes or primers from the sequences provided herein and screening a suitable nucleic acid source from individuals of the appropriate species.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

John Wiley & Sons, Inc., sections 2.10 and 6.3–6.4, incorporated herein by reference.

Preferably, each such hybridizing polynucleotide has a length that is at least 25%(more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expres-

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≧50 | 65° C.; 1xSSC -or- 42° C.; 1xSSC, 50% formamide | 65° C.; 0.3xSSC |
| B | DNA:DNA | <50 | $T_B$*; 1xSSC | $T_B$*; 1xSSC |
| C | DNA:RNA | ≧50 | 67° C.; 1xSSC -or- 45° C.; 1xSSC, 50% formamide | 67° C.; 0.3xSSC |
| D | DNA:RNA | <50 | $T_D$*; 1xSSC | $T_D$*; 1xSSC |
| E | RNA:RNA | ≧50 | 70° C.; 1xSSC -or- 50° C.; 1xSSC, 50% formamide | 70° C.; 0.3xSSC |
| F | RNA:RNA | <50 | $T_F$*; 1xSSC | $T_F$*; 1xSSC |
| G | DNA:DNA | ≧50 | 65° C.; 4xSSC -or- 42° C.; 4xSSC, 50% formamide | 65° C.; 1xSSC |
| H | DNA:DNA | <50 | $T_H$*; 4xSSC | $T_H$*; 4xSSC |
| I | DNA:RNA | ≧50 | 67° C.; 4xSSC -or- 45° C.; 4xSSC, 50% formamide | 67° C.; 1xSSC |
| J | DNA:RNA | <50 | $T_J$*; 4xSSC | $T_J$*; 4xSSC |
| K | RNA:RNA | ≧50 | 70° C.; 4xSSC -or- 50° C.; 4xSSC, 50% formamide | 67° C.; 1xSSC |
| L | RNA:RNA | <50 | $T_L$*; 2xSSC | $T_L$*; 2xSSC |
| M | DNA:DNA | ≧50 | 50° C.; 4xSSC -or- 40° C.; 6xSSC, 50% formamide | 50° C.; 2xSSC |
| N | DNA:DNA | <50 | $T_N$*; 6xSSC | $T_N$*; 6xSSC |
| O | DNA:RNA | ≧50 | 55° C.; 4xSSC -or- 42° C.; 6xSSC, 50% formamide | 55° C.; 2xSSC |
| P | DNA:RNA | <50 | $T_P$*; 6xSSC | $T_P$*; 6xSSC |
| Q | RNA:RNA | ≧50 | 60° C.; 4xSSC -or- 45° C.; 6xSSC, 50% formamide | 60° C.; 2xSSC |
| R | RNA:RNA | <50 | $T_R$*; 4xSSC | $T_R$*; 4xSSC |

‡: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†: SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete.
*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$ (° C.) = 2 (# of A + T bases) + 4 (# of G + C bases). For hybrids between 18 and 49 base pairs in length, $T_m$ (° C.) = 81.5 + 16.6 ($\log_{10}[Na^+]$) + 0.41 (% G + C) − (600/N), where N is the number of bases in the hybrid, and [$Na^+$] is the concentration of sodium ions in the hybridization buffer ([$Na^+$] for 1xSSC = 0.165 M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., sion control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No. 1555* (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

A protein of the present invention may have chemotactic or chemokinetic activity (e.g., act as a chemokine) for mammalian cells, including, for example, lymphocytes (such as, for example, thy mocytes, monocytes, neutrophils and T-cells), mast cells, eosinophils and/or endothelial cells. Murine L105 protein has been shown to be chemotactic for thymocytes, kidney mesangial cells and lymphocytes localized in lymph nodes. Human L105 protein shares these activities, as well as possessing other chemotactic and chemokinetic activities.

Chemotactic and chemokinetic proteins can be used to mobilized or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

The chemokinetic proteins of the present invention can also be used to block chemotaxis (e.g., by flooding the blood with the proteins and inducing "chemotactic paralysis" (i.e., there is no gradient for cells to move along, so no movement occurs)), such as to block inflammation.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

A protein has "chemokine activity" if it either (1) displays chemoattractant or chemotactic activity in a chemoattraction or chemotaxis assay (preferably an assay in which the corresponding species mature protein is active), or (2) displays biological activity in a factor-dependent cell proliferation assay (preferably an assay in which the corresponding species mature protein is active), or (3) displays activity in the induction of lymphokine production or effector function in an immune cell functional assay. Examples of effector function include, without limitation, tumoricidal activity, granule release, adhesion molecule expression, and the like.

Activity may be monitored using assays known in the art. Chemoattractant or chemotactic activity can also be measured in vivo by injecting protein at a particular site and performing a histological examination of the cell types that migrate to the site of injection.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Intersciece (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153: 1762–1768, 1994.

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunolgobulin and other molecules on B cells as well as antibodies able to bind the TCR and other molecules on T cells can be combined with the pharmaceutical compositon of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

Patent and literature references cited herein are incorporated by reference as if fully set forth.

What is claimed is:

1. A protein produced according to a process which comprises the steps of:
    (a) growing a culture of a cell in a suitable culture medium, wherein the cell is transformed with a polynucleotide operably linked to at least one expression vector sequence, wherein the polynucleotide is selected from the group consisting of:
        (aa) a polynucleotide of SEQ ID NO:3 from nucleotide 85 to nucleotide 519;
        (ab) a polynucleotide of SEQ ID NO:3 from nucleotide 124 to nucleotide 519;
        (ac) a polynucleotide encoding a protein comprising the amino acid sequence of SEQ ID NO:4;
        (ad) a polynucleotide encoding a protein comprising the amino acid sequence of SEQ ID NO:4 from amino acid 14 to amino acid 145;
        (ae) a polynucleotide encoding a protein comprising the amino acid sequence of SEQ ID NO:4 from amino acid 124 to amino acid 134; and
        (af) a polynucleotide comprising a fragment of the amino acid sequence of SEQ ID NO:4, the fragment comprising the amino acid sequence from amino acid 124 to amino acid 134; and
    (b) purifying the protein encoded by said polynucleotide from the culture.

2. The protein of claim 1, produced by the process wherein said transformed cell is an animal cell.

3. The protein of claim 1, produced by the process wherein said polynucleotide comprises the nucleotide sequence of SEQ ID NO:3 from nucleotide 85 to nucleotide 519.

4. The protein of claim 1, produced by the process wherein said polynucleotide comprises the nucleotide sequence of SEQ ID NO:3 from nucleotide 124 to nucleotide 519.

5. The protein of claim 1, produced by the process wherein said polynucleotide encodes a protein comprising the amino acid sequence of SEQ ID NO:4.

6. The protein of claim 1, produced by the process wherein said polynucleotide encodes a protein comprising the amino acid sequence of SEQ ID NO:4 from amino acid 14 to amino acid 145.

7. A composition comprising a protein, wherein said protein comprises an amino acid sequence selected from the group consisting of:
  (a) the amino acid sequence of SEQ ID NO:4;
  (b) the amino acid sequence of SEQ ID NO:4 from amino acid 14 to amino acid 145; and
  (c) fragments of the amino acid sequence of SEQ ID NO:4, each fragment comprising the amino acid sequence of SEQ ID NO:4 from amino acid 124 to amino acid 134;

the protein being substantially free from other proteins.

8. The composition of claim 7, further comprising a pharmaceutically acceptable carrier.

9. The composition of claim 7 wherein said protein comprises the amino acid sequence of SEQ ID NO:4.

10. The composition of claim 7 wherein said protein comprises the amino acid sequence of SEQ ID NO:4 from amino acid 14 to amino acid 145.

* * * * *